US009974310B2

(12) United States Patent
Campbell, Jr. et al.

(10) Patent No.: US 9,974,310 B2
(45) Date of Patent: May 22, 2018

(54) CERAMIC ADDITIVE FORMULATION AND METHOD OF MAKING

(71) Applicant: Microban Products Company, Huntersville, NC (US)

(72) Inventors: Alvin Lamar Campbell, Jr., Huntersville, NC (US); Nathan L. Fields, Concord, NC (US)

(73) Assignee: Microban Products Company, Huntersville, NC (US)

( * ) Notice: Subject to any disclaimer, the term of this patent is extended or adjusted under 35 U.S.C. 154(b) by 0 days. days.

(21) Appl. No.: 15/064,777

(22) Filed: Mar. 9, 2016

(65) Prior Publication Data
US 2017/0258092 A1    Sep. 14, 2017

(51) Int. Cl.
C04B 41/86 (2006.01)
C09D 5/14 (2006.01)
A01N 59/16 (2006.01)

(52) U.S. Cl.
CPC .............. A01N 59/16 (2013.01); C04B 41/86 (2013.01); C09D 5/14 (2013.01)

(58) Field of Classification Search
CPC .................................. C04B 41/86; C09D 5/14
See application file for complete search history.

(56) References Cited

U.S. PATENT DOCUMENTS

| 5,093,285 | A | * | 3/1992 | Murkens | C03C 8/02 |
| | | | | | 428/428 |
| 5,304,516 | A | | 4/1994 | Clifford | |
| 5,807,641 | A | | 9/1998 | Oku et al. | |
| 5,853,866 | A | | 12/1998 | Watanabe et al. | |
| 5,882,808 | A | | 3/1999 | Oku et al. | |
| 6,043,171 | A | | 3/2000 | Siebers et al. | |
| 6,303,183 | B1 | | 10/2001 | Wilczynski et al. | |
| 6,368,668 | B1 | | 4/2002 | Kobayashi et al. | |
| 6,383,646 | B1 | | 5/2002 | Tomioka et al. | |
| 6,514,622 | B1 | | 2/2003 | Hayakawa et al. | |
| 6,756,060 | B1 | | 6/2004 | Greenspan et al. | |
| 6,887,812 | B2 | | 5/2005 | Nenasheva et al. | |
| 7,250,178 | B2 | | 7/2007 | Olsson et al. | |
| 7,476,698 | B2 | | 1/2009 | Wagener et al. | |
| 7,488,442 | B2 | | 2/2009 | Matsumoto et al. | |
| 9,434,638 | B2 | | 9/2016 | Campbell, Jr. | |
| 9,446,980 | B2 | | 9/2016 | Campbell, Jr. | |
| 9,446,981 | B2 | | 9/2016 | Campbell, Jr. | |
| 2003/0118733 | A1 | * | 6/2003 | Jackson | A01N 25/24 |
| | | | | | 427/372.2 |
| 2003/0134107 | A1 | | 7/2003 | Machida et al. | |
| 2004/0103823 | A1 | | 6/2004 | Kurihara et al. | |
| 2005/0035500 | A1 | | 2/2005 | Matsumoto et al. | |
| 2005/0106336 | A1 | | 5/2005 | Ong et al. | |
| 2005/0158400 | A1 | | 7/2005 | Olsson et al. | |
| 2005/0196430 | A1 | | 9/2005 | Olsson et al. | |
| 2005/0252410 | A1 | | 11/2005 | Bujard et al. | |
| 2006/0048676 | A1 | | 3/2006 | Bujard | |
| 2006/0142413 | A1 | | 6/2006 | Zimmer et al. | |
| 2007/0110824 | A1 | | 5/2007 | Nageswaran | |
| 2007/0172661 | A1 | * | 7/2007 | Fechner | A01N 59/16 |
| | | | | | 428/409 |
| 2007/0275168 | A1 | | 11/2007 | Prochazka | |
| 2009/0104459 | A1 | | 4/2009 | Campbell, Jr. | |
| 2009/0117173 | A1 | | 5/2009 | Chen et al. | |
| 2012/0237686 | A1 | | 9/2012 | Chen et al. | |
| 2015/0010605 | A1 | | 1/2015 | Charme Delgado | |
| 2015/0030861 | A1 | | 1/2015 | Campbell, Jr. | |

FOREIGN PATENT DOCUMENTS

| CA | 2279785 A1 | 2/2000 |
| CN | 1615698 A | 5/2005 |
| CN | 1843995 A | 10/2006 |
| DE | 19834801 A1 | 2/2000 |
| DE | 202005006784 U1 | 9/2005 |
| JP | H111380 A | 1/1999 |
| WO | 0014029 A1 | 3/2000 |
| WO | 2010/126917 A1 | 11/2010 |
| WO | 2016094484 A1 | 6/2016 |

OTHER PUBLICATIONS

International Search Report and Written Opinion of corresponding application PCT/US2015/064634, dated Feb. 16, 2016, all enclosed pages cited.
PCT/US2008/054190; Form PCT/ISA/237; Written Opinion; dated Jun. 30, 2008; all enclosed pages cited.
PCT/US2008/054190; Form PCT/ISA/237; International Search Report; dated Jun. 30, 2008; all enclosed pages cited.
Supplementary Partial European Search Report for corresponding European Application EP 08730070, dated May 15, 2015, all enclosed pages cited.
Supplementary European Search Report for corresponding European Application EP 08730070, dated Oct. 5, 2015, all enclosed pages cited.
Ernest M. Levin, Carl R. Robbins and Howard F. McMurdie, "Phase Diagrams for Ceramists", Compiled at the National Bureau of Standards, Copyright 1964 by The American Ceramic Society, pp. 69 and 120, published in Columbus, Ohio.
ASTM International Designation: C 347-57 (Reapproved 1983), "Standard Test Method for Reflectance, Reflectivity, and Coefficient of Scatter of White Porcelain Enamels", copyright ASTM International, Annual Book of Standards, vol. 14.02, published Dec. 1983, pp. 733-735.
Herbert V. Oliveira et al., "Manual of Drying and Firing Porcelain Enamel", PEI-601, Version 1.2, published by the Porcelain Enamel Institute, Nashville, Tennessee, copyright 1996-1997, pp. 1-22.

(Continued)

Primary Examiner — Gina C Justice
(74) Attorney, Agent, or Firm — Nelson Mullins Riley & Scarborough LLP

(57) ABSTRACT

A method of making a ceramic glaze formulation having an antimicrobial property for use with a ceramic article. The method comprises fritting an antimicrobial formulation in a flux frit, providing least one unfritted antimicrobial component, providing a silver carrier in a glass matrix, and combining the flux frit, the at least one unfritted component, and the silver carrier in the glass matrix to form the ceramic glaze formulation. The silver carrier is combined at an addition rate based on a dry weight basis of the ceramic glaze formulation. A ceramic glaze additive formulation and ceramic glazed article are also provided.

19 Claims, No Drawings

(56) References Cited

OTHER PUBLICATIONS

Japanese Minister of International Trade and Industry and the Japanese Industrial Standards Committee, "Antimicrobial products—Test for antimicrobial activity and efficacy", Standardiztion Journal translated and published by the Japanese Standards Association, Reference No. JIS Z 2801 : 2000(E), published Dec. 20, 2000, Tokyo, Japan, pp. 1-11.
AATCC Committee RA31, "AATCC Test Method 100-1999, Antibacterial Finishes on Textile Materials: Assesment of", AATCC Technical Manual/2003, pp. 149-151.
Richard A. Eppler with Mimi Obstler, "Understanding Glazes", published by The American Ceramic Society, Westerville, Ohio, 2005, pp. 246, 247, 315.
ASTM International Designation: C286, "Standard Terminology Relating to Porcelain Enamel and Ceramic-Metal Systems", copyright ASTM International 1999 (Reapproved 2009) published Jan. 2010, West Conhohocken, PA, pp. 1 and 4.
The Edward Orton Jr. Ceramic Foundation, "Temperature Equivalent Chart for Orton Pyrometric Cones ( C)", www.ortonceramic.com, 2011.
Enamel; 9th Edition of Encyclopedia Britannica—free 9th Edition online Encyclopedia Britannica; vol. 8; all pages enclosed cited.
United States Patent and Trademark Office; Translation of "Antibacterial Enamel and Its Preparation Method" by Wenzhan Ding; Chinese Patent Application No. 1843995; translated Dec. 2012; Phoenix Translations; Elgin, Texas; all enclosed pages cited.
International Search Report and Written Opinion of corresponding application PCT/US2017/021070, dated May 23, 2017, all enclosed pages cited.

\* cited by examiner

CERAMIC ADDITIVE FORMULATION AND METHOD OF MAKING

FIELD OF THE INVENTION

The present invention relates generally to ceramic glazes, more particularly to a ceramic glaze additive formulation, a method of making the ceramic glaze additive formulation, and a ceramic glazed article.

BACKGROUND OF THE INVENTION

There is an increasing desire to have ceramic products have antimicrobial protection. For example, there is the desire for both household and commercial purposes for such ceramic products to be free of germs and bacteria.

Although consumers want such ceramic products to have this functional feature, consumers also do not want to sacrifice the appearance of such ceramic products. This includes the appearance of sanitary ware. Sanitary ware typically requires higher firing temperatures and a longer time period.

Sanitary ware requires a significant increase in the amount of zinc to give it the desired aesthetic color and appearance. Bismuth and zinc are two of the most difficult antimicrobial components to put into a glaze. Bismuth particles melt at a lower temperature than zinc, and zinc may not go into solution with the other components of the glaze. At the firing temperatures (about 2250° F.) and length of firing time (18-24 hours) for sanitary ware, both the bismuth and the zinc can cause problems with increased fluidity and dripping of the glaze. In not blended well, both can cause discolorations. Bismuth produces clear spots in a white glaze, and zinc produces whiter areas. There is also dimpling. Zinc can also react with chrome and tin to alter the resulting glaze color.

Thus, there is a need for a method and an additive formulation to overcome these problems yet while providing an energy efficient solution.

SUMMARY OF THE INVENTION

The present invention relates to a ceramic glaze additive formulation, a method of making the ceramic glaze additive formulation, and a ceramic glazed article.

A method of making a ceramic glaze formulation having an antimicrobial property for use with a ceramic article is provided. The method comprises fritting an antimicrobial formulation in a flux frit, wherein the flux frit is present in the ceramic glaze formulation in an amount of 45 weight % to 55 weight %, based on a dry weight basis of the ceramic glaze formulation; providing least one unfritted antimicrobial component; providing a silver carrier in a glass matrix; combining the flux frit, the at least one unfritted component, and the silver carrier in the glass matrix to form the ceramic glaze formulation; wherein the silver carrier is combined at an addition rate of at least 1 weight % based on a dry weight basis of the ceramic glaze formulation.

In another aspect of the invention, the method comprises fritting an antimicrobial formulation in a flux frit, wherein the flux frit is present in the ceramic glaze formulation in an amount of 1 weight % to 10 weight %, based on a dry weight basis of the ceramic glaze formulation; providing at least one unfritted antimicrobial component; providing a silver carrier in a glass matrix; combining the flux frit, the at least one unfritted antimicrobial component, and the silver carrier in the glass matrix to form the ceramic glaze formulation; wherein the silver carrier is added to the ceramic glaze formulation at an addition rate of at least 10 weight % based on a dry weight basis of the ceramic glaze formulation.

A ceramic glaze additive formulation is provided comprising: 0.1% to 1% by weight of silver carrier; 12% to 21% by weight of $Bi_2O_3$; 29% to 37% by weight of ZnO; and 45% to 55% by weight of flux frit, wherein a weight percentage is based upon the weight of the ceramic glaze additive formulation.

Another ceramic glaze additive formulation is provided comprising: 5% to 15% by weight of silver carrier; 80% to 90% by weight of ZnO; and 1% to 10% by weight of flux frit, wherein a weight percentage is based upon the weight of the ceramic glaze additive formulation.

A ceramic glazed article is provided comprising a ceramic glaze additive formulation applied on a surface of the ceramic article, the ceramic glaze additive formulation comprising: 0.1% to 1% by weight of silver carrier; 12% to 21% by weight of $Bi_2O_3$; 29% to 37% by weight of ZnO; and 45% to 55% by weight of flux frit, wherein a weight percentage is based upon the weight of the ceramic glaze additive formulation.

In still yet another aspect of the invention, another ceramic glazed article is provided comprising a ceramic glaze additive formulation comprising: 5% to 15% by weight of silver carrier; 80% to 90% by weight of ZnO; and 1% to 10% by weight of flux frit, wherein a weight percentage is based upon the weight of the ceramic glaze additive formulation.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DESCRIPTION OF THE PREFERRED EMBODIMENTS

The following description of the embodiments of the present invention is merely exemplary in nature and is in no way intended to limit the invention, its application, or uses. The present invention has broad potential application and utility, which is contemplated to be adaptable across a wide range of industries. The following description is provided herein solely by way of example for purposes of providing an enabling disclosure of the invention, but does not limit the scope or substance of the invention.

As used herein, the terms "microbe" or "microbial" should be interpreted to refer to any of the microscopic organisms studied by microbiologists or found in the use environment of a ceramic article or ceramic-glazed article. Such organisms include, but are not limited to, bacteria and fungi as well as other single-celled organisms such as mold, mildew and algae. Viral particles and other infectious agents are also included in the term microbe.

The term "antimicrobial" includes biostatic activity, i.e., where the proliferation of microbiological species is reduced or eliminated, and true biocidal activity where microbiological species are killed. For ease of discussion, this detailed description may make reference to bacteria and antibacterial agents. This method of presentation should not be interpreted as limiting the scope of the invention in any way. As well, "antimicrobial" and like terms should be interpreted as encompassing both microbe-killing as well as microbiostatic activities. That is, it herein is considered efficacious if an antimicrobial composition reduces the number of microbes on a substrate or it the composition retards the normal rate of microbial growth.

For ease of discussion, this description uses the terms microbes and antimicrobial to denote a broad spectrum activity (e.g. against bacteria and fungi). When speaking of efficacy against a particular microorganism or taxonomic rank, the more focused term will be used (e.g. antifungal to denote efficacy against fungal growth in particular).For ease of discussion, this description uses the terms microbes and antimicrobial to denote a broad spectrum activity (e.g. against bacteria and fungi). When speaking of efficacy against a particular microorganism or taxonomic rank, the more focused term will be used (e.g. antifungal to denote efficacy against fungal growth in particular).

Using the above example, it should be understood that efficacy against fungi does not in any way preclude the possibility that the same antimicrobial composition demonstrates efficacy against another class.

For example, discussion of the strong bacterial efficacy demonstrated by a disclosed embodiment should not be read to exclude the embodiment from also demonstrating antifungal activity. This method of presentation should not be interpreted as limiting the scope of the invention in any way.

Glazes are generally made from powdered glass combined with colored oxides of such elements as cobalt, chrome, manganese, or nickel. The powder mixture is suspended in water and applied to the ceramic surface by spraying, brushing, dipping, or other known application methods.

The suspension, or slip, in which the glaze is applied to the ceramic surface must have particular properties to ensure that the glaze is easy to apply, does not run during glaze application, and adheres well both when wet and after firing. These slip properties are often obtained by adding a small amount of clay to the suspension and by controlling both the amount of water in the slip as well as the size of the powder particles. Organic surface-active agents (e.g. surfactants, detergents) also can be added to the slip to improve its properties. Colors in glazes are controlled by adding coloring agents to the glassy components of the glaze.

A ceramic production glaze formulation is a combination of ceramic materials that have been developed for production application to specific ceramic articles. A ceramic glaze additive formulation is a combination of antimicrobial components that are combined in a ceramic production glaze formulation to result in an antimicrobial ceramic production glaze formulation.

The ceramic glaze additive formulation of the present invention comprises a fritted antimicrobial composition, an unfritted antimicrobial component(s), and a silver carrier in a glass matrix.

As used herein, "fritting" means melting an antimicrobial agent(s) or constituent(s) into a glass, quenching the glass to freeze the amorphous condition, and then grinding to a desired particle size. The fritted antimicrobial composition is a more homogeneous composition and allows higher amounts of the components than is acceptable in the oxide form. Using a flux frit as the entire source or the partial source of the antimicrobial components permits a much wider range of compositions. Fritting the composition creates an antimicrobial additive that is more easily combined with a base (untreated) glaze. The fritted material is also better tolerated in faster firing cycles with a reduction in surface defects due to varying firing cycles with a reduction in surface defects due to varying melting points and viscosities. The fritted material has fewer firing limitations because the dissociation of its components has already occurred during fritting.

The fritted antimicrobial composition comprises an antimicrobial selected from the group consisting of bismuth oxide ($Bi_2O_3$), zinc oxide (ZnO), and a combination thereof.

The unfritted components are selected from the group consisting of bismuth oxide ($Bi_2O_3$), zinc oxide (ZnO), and a combination thereof.

In an embodiment of the present invention, a first ceramic glaze formulation is provided. The first ceramic glaze formulation comprises 0.1% to 1% by weight of silver carrier; 12% to 21% by weight of $Bi_2O_3$; 29% to 37% by weight of ZnO; and 45% to 55% by weight of flux frit, based upon the weight of the ceramic glaze formulation.

In an embodiment of the present invention, a second ceramic glaze formulation is provided. The second ceramic glaze formulation comprises 5% to 15% by weight of silver carrier; 80% to 90% by weight of ZnO; and 1% to 10% by weight of flux frit, based upon the weight of the ceramic glaze formulation.

In accordance with the present invention, a method of making a ceramic glaze having an antimicrobial property for use with a ceramic article is provided.

Those skilled in the art recognize that the production process of ceramic products may vary from that which is presented below, and that the ceramic glazing process disclosed herein is adaptable to other substrates.

In a first embodiment of the method, the method generally comprises fritting an antimicrobial formulation in a flux frit, wherein the flux frit is present in the ceramic glaze formulation in an amount of 45 weight % to 55 weight %, based on a dry weight basis of the ceramic glaze formulation; providing at least one unfritted antimicrobial component; providing a silver carrier in a glass matrix; combining the flux frit, the at least one unfritted antimicrobial component, and the silver carrier in the glass matrix to form the ceramic glaze formulation. The silver carrier is combined at an addition rate of at least 1 weight % based on a dry weight basis of the glaze formulation.

In a second embodiment of the method, the method generally comprises fritting an antimicrobial formulation in a flux frit, wherein the flux frit is present in the ceramic glaze additive formulation in an amount of 1 weight % to 10 weight %, based on a dry weight basis of the ceramic glaze formulation; providing at least one unfritted antimicrobial component; providing a silver carrier in a glass matrix; combining the flux frit, the at least one unfritted antimicrobial component, and the silver carrier in the glass matrix to form the ceramic glaze formulation. The silver carrier is combined at an addition rate of at least 10 weight % based on a dry weight basis of the ceramic glaze formulation.

There are numerous methods by which the silver carrier can be combined with the flux frit. The silver carrier can be mixed into the frit. It may require a larger amount of silver ions on the surface of the carrier. Another method by which the silver carrier can be combined with the flux frit is by a treatment material such as a chemical bath. It is possible to preferentially put silver into a glass matrix such that it is on the surface of the carrier.

In an aspect of the method, the antimicrobial formulation comprises an antimicrobial selected from the group consisting of zinc oxide, bismuth oxide, titanium oxide, tin oxide, silver compound, and a combination thereof In a preferred aspect of the invention, the antimicrobial formulation comprises an antimicrobial selected from the group consisting of bismuth oxide, zinc oxide, and a combination thereof. It was surprisingly found that there is a synergistic effect with zinc oxide and bismuth oxide in certain combinations when used in the method of this invention.

In another aspect of the method, the flux frit further comprises a glass former. The glass formers are typically glass constituents having no efficacious history.

In an aspect of the method, $Bi_2O_3$ is present in the flux frit in a range of 50% to 56% by weight, preferably in a range of 52% to 54% by weight, of the flux frit.

In an aspect of the invention, ZnO is present in the flux frit in a range of 1% to 5% by weight, of the flux frit.

In an aspect of the first embodiment of the method, unfritted $Bi_2O_3$ is present in the ceramic glaze formulation in a range of 12% to 20% by weight, preferably in a range of 14% to 18% by weight, of the ceramic glaze formulation.

In an aspect of the first embodiment of the method, unfritted ZnO is present in the ceramic glaze formulation in a range of 29% to 37% by weight, preferably in a range of 31% to 35% by weight, of the ceramic glaze formulation.

In an aspect of the second embodiment of the method, unfritted $Bi_2O_3$ is present in the ceramic glaze formulation in a range of 0% to 5% by weight, preferably 0% by weight, of the ceramic glaze formulation.

In an aspect of the second embodiment of the method, unfritted ZnO is present in the ceramic glaze formulation in a range of 80% to 90% by weight, preferably in a range of 83% to 87% by weight, of the ceramic glaze formulation.

In another embodiment of the present invention, a ceramic article is provided. The ceramic glazed article comprises a fritted antimicrobial composition comprising an antimicrobial selected from the group consisting of bismuth oxide, zinc oxide, and a combination thereof; and a silver carrier in a glass matrix.

In an aspect of a first embodiment of the invention, the bismuth oxide is present in a range of 59% to 68% by weight of the ceramic glaze formulation, zinc oxide is present in an amount of 30% to 40% by weight of the ceramic glaze formulation, and the silver carrier is present in a range of 0.1% to 1% by weight of the ceramic glaze formulation.

In an aspect of a second embodiment of the invention, the bismuth oxide is present in a range of 0% to 10% by weight of the ceramic glaze formulation, zinc oxide is present in an amount of 80% to 90% by weight of the ceramic glaze formulation, and the silver carrier is present in a range of 5% to 15% by weight of the ceramic glaze formulation.

The ceramic article of the present invention is any article having a ceramic glaze including, but not limited to, toilets, bidets, washbasins, towel rails, soap holders, toilet roll holders, water control fixtures (e.g., hot and cold water handles), and tiles.

These ceramic glaze additive formulations were surprisingly found to achieve the appearance and color that is needed of the finished ceramic article yet overcome energy and cost inefficiencies associated with only having a fritted antimicrobial composition. Fritting is energy intensive due to the energy required with melting, cooling, grinding and any size separation.

The present invention surprisingly solves the need of making faster fired ceramic articles. The term "faster fired" refers to a shorter time required for the ceramic article to cycle through the kiln while maintaining the required properties and quality produced using the longer firing time. For example, the method reduces the firing time for various components of the glaze formulation. When subjected to heat, a ceramic formulation goes through various combinations of time and temperature (heat treatment) in a kiln to develop a vitreous or crystalline bond necessary to provide the properties associate with a ceramic material. This heat treatment (combination of time and temperature) is necessary to remove those materials which are given off at various points within the kiln. Examples of these are water of formation, chemical water, carbonates, phosphates, and all included organic materials. These are also known as "products of combustion" or "loss on ignition". Sufficient time must be provided for these materials to be expelled before the next time/temperature combination is reached. When the components of a glaze formulation are added as frit(s), all or part of the materials that would give off water, carbonates, etc., have been pre-fired to a glassy state, quenched, and ground to the proper size (frit), there is no reason to slow down the heat treatment. All of the reactions for the "products of combustion" have taken place during the fritting operation. Additionally, the method eliminates surface texture problems such as the hammered look that is seen on glossy glazes when an antimicrobial is added as a mixture of components.

In still yet another aspect of the method, it was surprisingly found that when a ceramic production glaze formulation, that is to be applied to a ceramic production substrate or article, comprises about 2 weight % to about 12 weight % on a dry weight basis of zinc oxide that it is possible to reduce the amount of zinc oxide in the antimicrobial addition. Thus, as a feature of the present invention, the amount of zinc oxide can range from 0 weight % to 10 weight % in the antimicrobial formulation depending upon the amount of zinc oxide already present in the ceramic production glaze formulation. This is as a component of the antimicrobial formulation that is then added to the ceramic production glaze formulation at 4 weight % to 10 weight % on a dry weight basis.

The fritting method of the present invention can be used to implement the different antimicrobial combinations into an untreated glaze or as an application of these materials in an aqueous solution or organic carrier onto the top surface of an unfired glaze.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A method of making a ceramic glaze formulation having an antimicrobial property for use with a ceramic article, the method comprising:
   fritting an antimicrobial formulation in a flux frit, wherein the flux frit is present in the ceramic glaze formulation in an amount of 45 weight % to 55 weight %, based on a dry weight basis of the ceramic glaze formulation;
   providing least one unfritted antimicrobial component;
   providing a silver carrier in a glass matrix;

combining the flux frit, the at least one unfritted component, and the silver carrier in the glass matrix to form the ceramic glaze formulation;
wherein the silver carrier is combined at an addition rate of at least 1 weight % based on a dry weight basis of the ceramic glaze formulation, and
wherein the unfritted component is unfritted $Bi_2O_3$ present in the ceramic glaze formulation in a range of 12% to 20% by weight of the ceramic glaze formulation.

2. The method according to claim 1, wherein the flux frit comprises an antimicrobial selected from the group consisting of zinc oxide, bismuth oxide, titanium oxide, tin oxide, silver compound, and a combination thereof.

3. The method according to claim 2, wherein the flux frit comprises an antimicrobial selected from the group consisting of bismuth oxide, zinc oxide, and a combination thereof.

4. The method according to claim 3, wherein the flux frit further comprises a glass former.

5. The method according to claim 3, wherein $Bi_2O_3$ is present in a range of 50% to 56% by weight of the flux frit.

6. The method according to claim 5, wherein $Bi_2O_3$ is present in a range of 52% to 54% by weight of the flux frit.

7. The method according to claim 3, wherein ZnO is present in a range of 1% to 5% by weight of the flux frit.

8. The method according to claim 1, wherein the unfritted component is selected from the group consisting of zinc oxide, bismuth oxide, titanium oxide, tin oxide, silver compound, and a combination thereof.

9. The method according to claim 1, wherein the unfritted component is unfritted $Bi_2O_3$ present in the ceramic glaze formulation in a range of 14% to 18% by weight of the ceramic glaze formulation.

10. The method according to claim 8, wherein the unfritted component is unfritted ZnO present in the ceramic glaze formulation in a range of 29% to 37% by weight of the ceramic glaze formulation.

11. The method according to claim 10, wherein the unfritted component is unfritted ZnO present in the ceramic glaze formulation in a range of 31% to 35% by weight of the ceramic glaze formulation.

12. A method of making a ceramic glaze formulation having an antimicrobial property for use with a ceramic article, the method comprising:
fritting an antimicrobial formulation in a flux frit, wherein the flux frit is present in the ceramic glaze formulation in an amount of 1 weight % to 10 weight %, based on a dry weight basis of the ceramic glaze formulation;
providing at least one unfritted antimicrobial component;
providing a silver carrier in a glass matrix;
combining the flux frit, the at least one unfritted antimicrobial component, and the silver carrier in the glass matrix to form the ceramic glaze formulation;
wherein the silver carrier is added to the ceramic glaze formulation at an addition rate of at least 10 weight % based on a dry weight basis of the ceramic glaze formulation;
wherein the unfritted component is selected from the group consisting of zinc oxide, bismuth oxide, titanium oxide, tin oxide, silver compound, and a combination thereof; and
wherein the unfritted component is unfritted ZnO present in the ceramic glaze formulation in a range of 80% to 90% by weight of the ceramic glaze formulation.

13. The method according to claim 12, wherein the flux frit comprises an antimicrobial selected from the group consisting of zinc oxide, bismuth oxide, titanium oxide, tin oxide, silver compound, and a combination thereof.

14. The method according to claim 13, wherein the flux frit comprises an antimicrobial selected from the group consisting of bismuth oxide, zinc oxide, and a combination thereof.

15. The method according to claim 14, wherein the flux frit further comprises a glass former.

16. The method according to claim 14, wherein $Bi_2O_3$ is present in a range of 50% to 56% by weight of the flux frit.

17. The method according to claim 16, wherein $Bi_2O_3$ is present in a range of 52% to 54% by weight of the flux frit.

18. The method according to claim 14, wherein ZnO is present in a range of 1% to 5% by weight of the flux frit.

19. The method according to claim 12, wherein the unfritted component is unfritted ZnO present in the ceramic glaze formulation in a range of 83% to 87% by weight of the ceramic glaze formulation.

* * * * *